US00PP09424P

United States Patent [19]

Jepsen

[11] Patent Number: Plant 9,424

[45] Date of Patent: Jan. 9, 1996

[54] KALANCHOE PLANT NAMED 'JAQUELINE'

[75] Inventor: Knud Jepsen, Hinnerup, Denmark

[73] Assignee: Knud Jepsen A/S, Hinnerup, Denmark

[21] Appl. No.: 376,931

[22] Filed: Jan. 23, 1995

[51] Int. Cl.[6] ..... A01H 5/00

[52] U.S. Cl. ..... Plt./87.15

[58] Field of Search ..... Plt./87.15

*Primary Examiner*—James R. Feyrer

*Attorney, Agent, or Firm*—Foley & Lardner

[57] ABSTRACT

A Kalanchoë plant named Jaqueline particularly characterized by its large and luminous flowers; distinctive and intense petal color; green leaves; and good keeping quality.

1 Drawing Sheet

The present invention relates to a new and distinct cultivar of Kalanchoë plant, botanically known as Kalanchoë, and referred to by the cultivar name Jaqueline.

The new cultivar was referred to during the breeding and selection process by the designation No. KJ 9/89-12A and is a product of a planned breeding program. The basic objective of the breeding program was to create a new Kalanchoë cultivar having large and luminous flowers, green leaves and a good keeping quality.

The new cultivar was originated from a cross made in a controlled breeding program in Hinnerup, Denmark. The female or seed parent was an undesignated and proprietary selection and the male or pollen parent was a cultivar designated Pollux. Jaqueline was discovered and selected by the inventor as a flowering plant within the progeny of the stated cross in a controlled environment in Hinnerup, Denmark.

Asexual reproduction of the new cultivar was first accomplished by the inventor in April 1989 in Hinnerup, Denmark. Asexual reproduction of the new cultivar by stem cuttings, as performed by the inventor at Hinnerup, Denmark, has demonstrated that the combination of characteristics as herein disclosed for the new cultivar are firmly fixed and retained through successive generations of asexual reproduction.

Jaqueline has not been observed under all possible environmental conditions. The phenotype may vary with variations in environment such as temperature, light intensity and day length without a change in the genotype of the plant. The following observations, measurements and values describe the new cultivar as grown in Hinnerup, Denmark under greenhouse conditions which closely approximate those generally used in commercial practice.

The following traits have been repeatedly observed and are determined to be basic characteristics of Jaqueline, which in combination, distinguish this Kalanchoë as a new and distinct cultivar:

1. Large and luminous flowers.
2. Distinctive and intense petal color.
3. Green leaves.
4. Good keeping quality.

Jaqueline is principally distinguished from Pollux by its color and a much longer keeping quality. The accompanying photographic drawings show a typical specimen plant of the new cultivar. The colors appearing in the photograph are as true as possible with color illustrations of this type.

Figure 1:
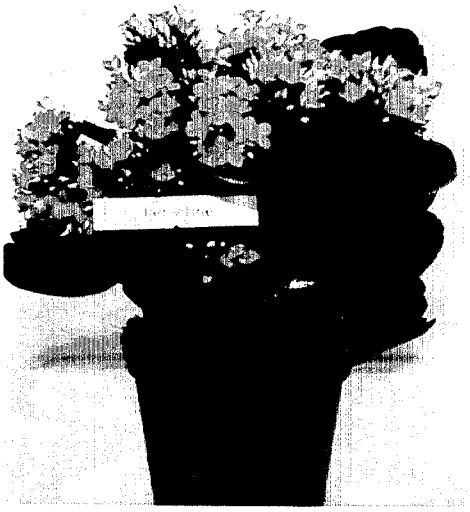
FIG. 1 is a sideview of the specimen plant showing its large and luminous flowers that have a distinctive color.
Figure 2:
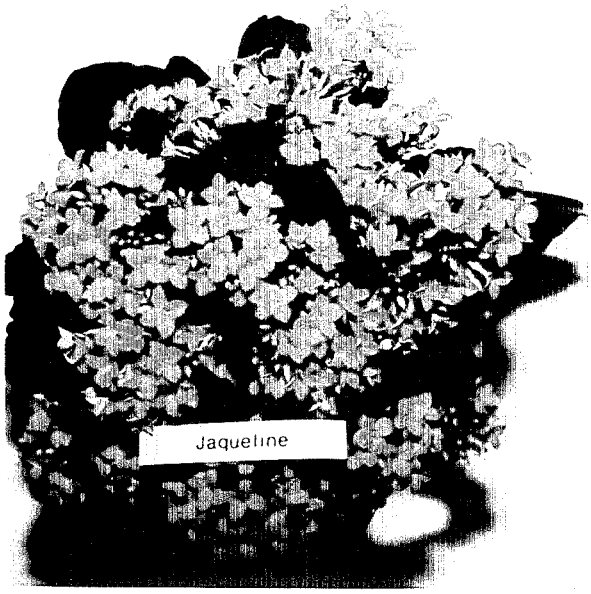
FIG. 2 is a topview of the new cultivar.
Figure 3:
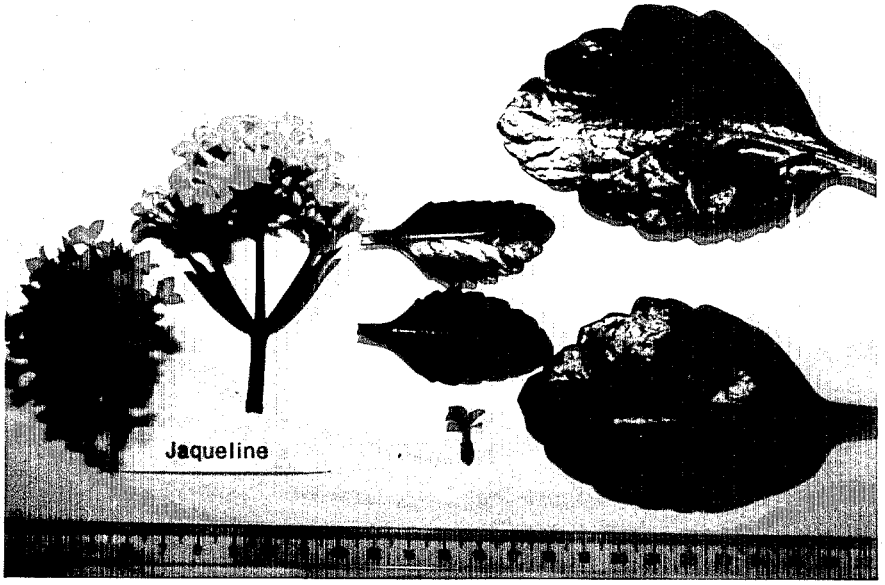
FIG. 3 is a close-up of the leaves and flowers of Jaqueline.

In the following description, color references are made to The Royal Horticultural Society Colour Chart (RHS), except where general colors of ordinary significance are referred to. Color values were taken under diffuse natural light conditions on a overcast day at approximately 12:00 a.m. in Hinnerup, Denmark.

Botanical classification:

*Commercial.*—Kalanchoë cv. Jaqueline.

Parentage:

*Male parent.*—Pollux.

*Female parent.*—Proprietary and undesignated selection.

Propagation: The new cultivar holds its distinguishing characteristics through successive propagations by leaf cuttings and by division of shoots.

*Type cuttings.*—Top shoot.

*Time to root.*—Ten (10) days.

*Rooting habit.*—Branched roots produced from callus.

Plant description:

*Form.*—Compact plant with multiple flowering shoots. Height ca. 25 cm. Diameter ca. 20 cm.

*Habit of growth.*—Upright growth, medium internodes, short and upright flowering shoots.

*Foliage description.*—Medium leaves with short petioles. The leaf size is reduced when the floral stage is induced.

*Size.*—Vegetative leaf is approximately 10.5 cm×8 cm. The leaves produced by flowering plants are approximately 7.5 cm×4.5 cm.

*Shape.*—Oval with an obtuse leaf tip.

*Texture.*—Glabrous.

*Margin.*—Undulate.

*Color.*—Young foliage: (topside): RHS 141A; (underside): RHS 138A. Mature foliage: (topside): RHS 136B; (underside): RHS 137B.

Flowering description:

*Flowering habits.*—Flowering is induced by short day length. Cymes are formed.

*Natural flowering season.*—Winter and spring. Flowering time under controlled day length at 20° C. in summer is 9.5 weeks. In winter (with artificial lighting) at 20° C. in the flowering time is 10.5 weeks. Flowering time depends on temperature, light intensity and other growing conditions.

*Flower buds.*—Dusty pink bud color. RHS 58B. Size: 1.5×0.3 cm just before anthesis. Shape: Narrow. Rate of opening: 50% open 1.5 weeks after first open flower.

*Flowers borne.*—The flowers are borne in dishasial cymes developing from leaf axils. The main inflorescences are branched into one central and 2–4 minor cymes during development.

*Quantity of flowers.*—8–10 head bunches with 24–45 flowers in 10–20 secondary bunches with 8–12 flowers (unpinched plants).

*Petals.*— Shape: Round obovate with cuspidate leaf tips. Color: Topside when opening: RHS 66A. fading to RHS 66B. Underside: RHS 66B. Number and size of petals: Four (4). Size of flowers: The petals measure 0.9 cm in diameter and the total flower diameter is 1.8 cm.

*Reproductive organs.*— Stamens: Eight (8) in number. Anthers shape: Slightly oblong. Filament color: Yellow/green. Pollen color: Yellow. Pistils: Stigma: Round. Style color: White. Ovaries: Four (4) ovaries each measuring 0.5 cm×0.1 cm. The ovaries are light green and superior (hypogonous).

Disease resistance: No known Kalanchoë diseases observed to date. Resistance not observed.

General observations: Jaqueline produces high-quality plants without pinching when grown in 9–10 cm pots with one cutting per pot. For larger 12 cm pots high-quality plants are produced when three cuttings or one pinched cutting is used per pot.

It is claimed:

1. A new and distinct Kalanchoë plant named Jaqueline, as described and illustrated.

* * * * *